(12) United States Patent
Marcoux et al.

(10) Patent No.: US 7,888,546 B2
(45) Date of Patent: Feb. 15, 2011

(54) WOUND DRESSING, INGREDIENT DELIVERY DEVICE AND IV HOLD-DOWN, AND METHOD RELATING TO SAME

(75) Inventors: Michael G. Marcoux, Wyoming, MI (US); David R. Johnson, Granger, IN (US); Steven R. Klemm, Grand Rapids, MI (US)

(73) Assignee: Corium International, Inc., Menlo Park, CA (US)

(*) Notice: Subject to any disclaimer, the term of this patent is extended or adjusted under 35 U.S.C. 154(b) by 422 days.

(21) Appl. No.: 10/563,340

(22) PCT Filed: Jul. 2, 2004

(86) PCT No.: PCT/US2004/021521

§ 371 (c)(1),
(2), (4) Date: Jul. 24, 2006

(87) PCT Pub. No.: WO2005/007020

PCT Pub. Date: Jan. 27, 2005

(65) Prior Publication Data

US 2007/0106195 A1   May 10, 2007

Related U.S. Application Data

(60) Provisional application No. 60/484,711, filed on Jul. 3, 2003, provisional application No. 60/508,088, filed on Oct. 2, 2003, provisional application No. 60/570,666, filed on May 13, 2004.

(51) Int. Cl.
*A61F 13/00* (2006.01)
*A61F 15/00* (2006.01)
*A61F 13/02* (2006.01)
*A61L 15/00* (2006.01)

(52) U.S. Cl. .............................. 602/52; 602/41; 602/42; 602/43; 602/47; 602/54; 602/55; 128/888; 604/304; 604/307; 604/308; 424/443; 424/445

(58) Field of Classification Search .............. 602/41–59; 128/888; 604/304–308; 424/443–449
See application file for complete search history.

(56) References Cited

U.S. PATENT DOCUMENTS

| | | |
|---|---|---|
| 4,372,303 A | 2/1983 | Grossmann et al. |
| 4,485,809 A | 12/1984 | Dellas |
| 4,598,004 A | 7/1986 | Heinecke |
| 4,600,001 A | 7/1986 | Gilman |
| 4,614,183 A | 9/1986 | McCracken et al. |
| 4,753,232 A | 6/1988 | Ward |
| 4,787,380 A | 11/1988 | Scott |
| 4,861,665 A | 8/1989 | Kasahara |
| 4,875,473 A | 10/1989 | Alvarez |
| 4,884,563 A | 12/1989 | Sessions |
| 4,915,228 A | 4/1990 | Johns |

(Continued)

*Primary Examiner*—Patricia M Bianco
*Assistant Examiner*—Brandon Jackson
(74) *Attorney, Agent, or Firm*—Price, Heneveld, Cooper, DeWitt & Litton, LLP (57) ABSTRACT

An adhesive device used as a wound dressing, ingredient delivery device or IV hold-down in which inadvertent edge release of these devices along the periphery of the polymeric film layer is minimized when the handling layer, which is adhered to the polymeric film layer, is removed after application of the polymeric film layer to the patient.

31 Claims, 5 Drawing Sheets

U.S. PATENT DOCUMENTS

| | | | |
|---|---|---|---|
| 4,917,112 | A | 4/1990 | Kalt |
| 4,917,929 | A | 4/1990 | Heinecke |
| RE33,353 | E | 9/1990 | Heinecke |
| 4,963,045 | A | 10/1990 | Willcox |
| 5,000,172 | A | 3/1991 | Ward |
| RE33,727 | E | 10/1991 | Sims |
| 5,088,483 | A | 2/1992 | Heinecke et al. |
| 5,160,315 | A | 11/1992 | Heinecke et al. |
| 5,336,162 | A | 8/1994 | Ota et al. |
| 5,413,567 | A | 5/1995 | Barth et al. |
| 5,437,622 | A | 8/1995 | Carion |
| 5,520,629 | A | 5/1996 | Heinecke et al. |
| 5,531,855 | A | 7/1996 | Heinecke et al. |
| 5,599,289 | A | 2/1997 | Castellana |
| 5,722,943 | A | 3/1998 | Sessions et al. |
| 5,738,642 | A | 4/1998 | Heinecke et al. |
| 5,749,842 | A | 5/1998 | Cheong et al. |
| 5,931,800 | A | 8/1999 | Rasmussen et al. |
| 5,951,505 | A | 9/1999 | Gilman et al. |
| 5,994,613 | A | 11/1999 | Cummings et al. |
| 6,008,429 | A | 12/1999 | Ritger |
| 6,014,585 | A | 1/2000 | Stoddard |
| 6,043,406 | A | 3/2000 | Sessions et al. |
| 6,096,942 | A | 8/2000 | Hack |
| 6,121,508 | A | 9/2000 | Bischof et al. |
| 6,124,522 | A | 9/2000 | Schroeder |
| 6,225,521 | B1 | 5/2001 | Gueret |
| 6,252,129 | B1 | 6/2001 | Coffee |
| 6,346,653 | B1 | 2/2002 | Sessions et al. |
| D454,955 | S * | 3/2002 | Dunshee et al. ............ D24/189 |
| 6,436,432 | B2 * | 8/2002 | Heinecke et al. ............ 424/443 |
| 6,685,682 | B1 * | 2/2004 | Peterson et al. ............ 604/307 |
| 6,923,320 | B2 | 8/2005 | Grossman |
| 7,135,606 | B1 * | 11/2006 | Dozier et al. ................ 602/57 |
| 2002/0107466 | A1 | 8/2002 | Faasse, Jr. |
| 2004/0004014 | A1 | 1/2004 | Grossman |
| 2005/0256439 | A1 * | 11/2005 | Grossman .................... 602/57 |

* cited by examiner

WOUND DRESSING, INGREDIENT DELIVERY DEVICE AND IV HOLD-DOWN, AND METHOD RELATING TO SAME

CLAIM OF PRIORITY

Applicant claims priority to provisional application Ser. No. 60/484,711, filed Jul. 3, 2003, provisional patent application Ser. No. 60/508,088, filed Oct. 2, 2003, and provisional patent application Ser. No. 60/570,666, filed May 13, 2004.

BACKGROUND OF THE INVENTION

The present invention relates to adhesive devices used as wound dressings, ingredient delivery devices and IV hold-downs.

Wound dressing and IV hold-downs in particular comprise a layer of polymeric film having an adhesive layer on one side thereof, which is protected during storage and handling by a release liner. United States Patent Publication 2002/0107466 A1 discloses such devices which also have a handling member adhered to the non-adhesive coated side of the polymeric film by means of a pressure sensitive adhesive. The pressure sensitive adhesive used between the handle and the polymeric film is less aggressive than the pressure sensitive adhesive used on the underside of the polymeric film, such that once the polymeric film is applied to a patient's skin or mucosa, the handle can be peeled away without peeling the polymeric film away from the patient's skin.

Experience has shown that regardless of differences in adhesive strength between the skin or mucosa adhesive and the handle adhesive, there is a tendency for the edge of the polymeric film to lift away from the user's skin or mucosa when the handle member is peeled away from the back of the polymeric film. This same tendency is observed in the wound dressing disclosed in U.S. Pat. No. 6,169,224, where the handling member is sealed to the polymeric film by a heat activated adhesive.

SUMMARY OF THE INVENTION

In the various aspects of the present invention, inadvertent edge release caused by peeling the handle member away from the polymeric film can be minimized by the following methods or combinations thereof:
1. minimizing the electrostatic charge buildup in the localized area of the polymeric film beneath the handle, as the handle is peeled away from the film; and/or
2. decreasing the mechanical advantage of the handle relative to the thin film.

In various different preferred aspects of the invention, either or both of these are accomplished by:
1. interrupting the continuity of contact between the handle and the underlying surface of the polymeric film to which the handle is adhered, said adherence either being due to electrostatic attraction or to the use of an adhesive layer on the underside of the handle;
2. placing an anti-static ingredient in one of, the adhesive coating on the underside of the polymeric film, or in an anti-static coating on the upper or lower surface of the polymeric film itself, with the anti-static agent preferably being located in an adhesive layer on the underside of the polymeric film;
3. removing at least a portion of the periphery of the handle layer, or of the adhesive layer on the underside of the handle if one issued, so that it does not extend to the periphery of the polymeric film layer upon which the handle layer resides; and/or
4. reducing the surface area of the adhesive coating disposed on the periphery of handle.

In another aspect of the invention, an inwardly-directed thumb tab, oriented at an obtuse angle with respect to the edge of the handle in the direction in which the handle is pulled, is provided to facilitate peeling of the handle away from the polymeric film. Such a thumb tab enhances the ease with which the handle is peeled away from the polymeric film. The thumb tab starts the peeling at such an angle that the tendency of the handle to lift the underlying polymeric film away from the patient's skin or mucosa is minimized.

These and other objects, features and advantages of the invention will be more fully understood and appreciated by reference to the written specification and appended drawings.

DETAILED DESCRIPTION OF PREFERRED EMBODIMENT

Introduction

The term "dressing" as used herein is to be understood to include wound dressings, IV hold-downs and transdermal, dermal, transmucosal and mucosal delivery systems. The various preferred embodiments disclosed herein have many components or similar components in common, which are described in this Introduction using numbers which are common to all embodiments. The differing embodiments, and the similar elements thereof, are distinguished by adding the letters a-j.

Figure 1:
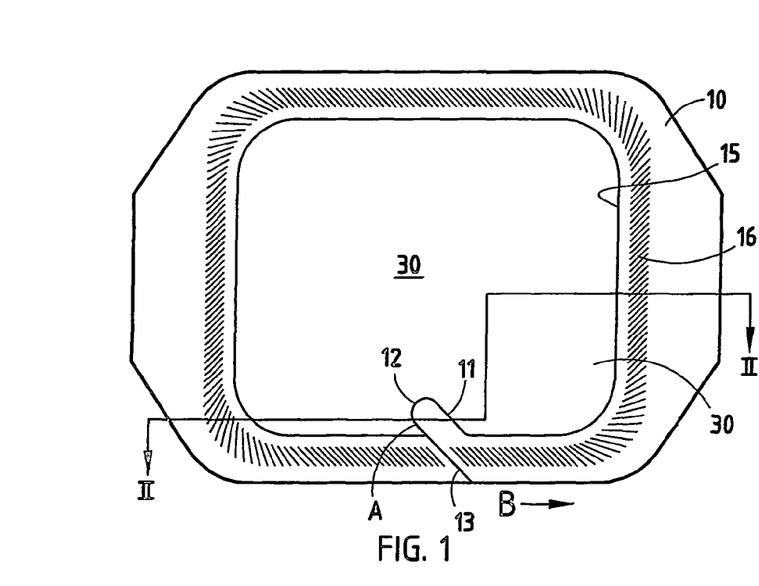
FIG. 1 is a plan view of a wound dressing, ingredient delivery device, or IV hold-down in accordance with a first embodiment of the present invention.
Figure 2:
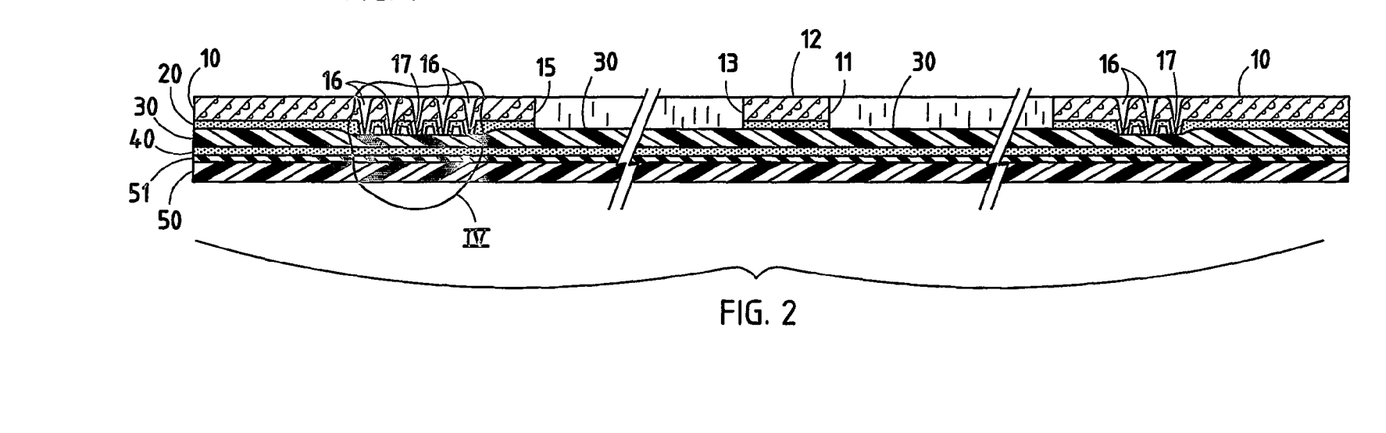
FIG. 2 is a cross sectional view of the wound dressing, ingredient delivery device, or IV hold-down of FIG. 1, taken along line II-II of FIG. 1.
Figure 3:
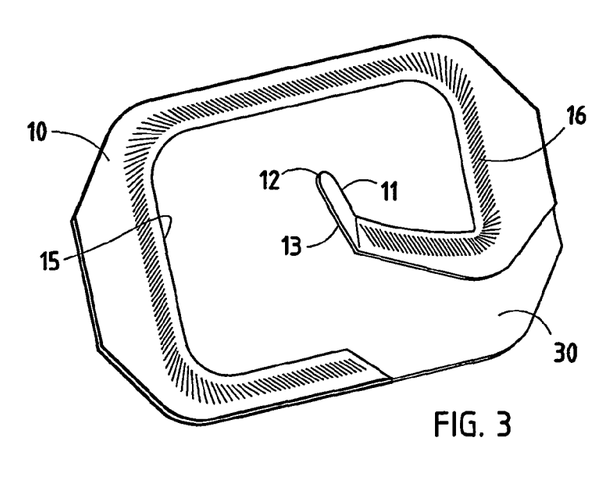
FIG. 3 is a perspective view of a wound dressing, ingredient delivery device, or IV hold-down of FIG. 1, with the handle being removed.

In the various preferred embodiments, the basic elements of a device in accordance with the present invention comprise a handle 10 having either an adhesive coating 20 on the undersurface thereof or being electrostatically adhered to an underlying polymeric film 30, and preferably having an inwardly-projecting thumb tab 11 (FIGS. 1-3). Handle 10 is applied to the non-adhesive coated surface of a polymeric film 30 having a pressure sensitive adhesive layer 40 on the undersurface thereof. Adhesive layer 40 is protected during handling and storage by a release liner 50 having a silicone coating layer 51. In use, release liner 50 is removed from the assembled polymeric film 30 and handle 10, and handle 10 is then used to manipulate the polymeric film and place it on the patient. Once the polymeric film as been applied to the patient, the user grasps inwardly-projecting thumb tab 11 on handle 10 and peels handle 10 away from the applied polymeric film 30.

Inadvertent edge release caused by removal of the handle 10 is minimized by any one or any combination of the following:

1. the angle at which thumb tab 11 projects from handle 10;
2. by minimizing the build up of localized electrostatic charge on the polyurethane film as the handle is removed; and/or
3. decreasing the mechanical advantage of handle 10 relative to film 30.

Objects 2 and 3 are accomplished by any one or any combination of the following:

1. interrupting the continuity of contact between the handle and the underlying non-adhesively coated surface of the polymeric film;
2. placing an anti-static ingredient in one of, the adhesive coating on the underside of the polymeric film, or in an anti-static coating on the upper or lower surface of the polymeric film itself, with the anti-static agent preferably being located in the adhesive layer on the underside of the polymeric film;
3. removing at least a portion of the periphery of the handle layer, or of the adhesive layer on the underside of the handle, if one issued, so that it does not extend to the periphery of the polymeric film layer upon which the handle layer resides; and/or
4. reducing the surface area of the adhesive coating disposed on the periphery of handle.

Handle 10 is preferably made of a stiffer and generally thicker material than that of polymeric film 30. Typical of such materials are plastic or paper material. Useable plastics include polyesters, polycarbonates, PVC's, polyurethanes, polyethylene vinyl acetates, polyester copolymers, polyethylenes, and polypropylenes. In the preferred embodiment a silicone coated paper 50, with a silicone coating 51 on the upper surface thereof, is used.

In FIG. 2, the undersurface of each handle 10 is coated with an optional adhesive layer 20, preferably a pressure sensitive adhesive which is moderately aggressive with respect to polymeric film 30, but which does not adhere or adheres less aggressively to either the silicone coating 51 on release liner 50 or to human skin. In this way, a user can readily fold back an end portion of release liner 50 to expose an end of handle 10, and the exposed end can then be used to peel film 30 away from release liner 50. The adhesive of layer 20 is "moderately aggressive" in that handle 10 remains attached to polymeric film 30 when it is peeled away from release liner 50, and while it is being handled and applied to the patient's skin. However, adhesive 20 is less aggressive with respect to its adhesion to polymeric film 30, than is the adhesion of layer 40 on the undersurface of polymeric film 30 toward human skin or mucosa. As a result, handle 10 can be peeled away from polymeric film 30, once film 30 is applied to the patient.

One type of adhesive which we have found useful for layer 20 on the undersurface of handle 10 is a low tack removable acrylate-based adhesive with a peel adhesive level of approximately three ounces. Other useful adhesives include, but are not limited to, silicone, urethane, synthetic rubber and natural rubber. Adhesives of this type can be formulated to have essentially no or very little adhesion to the human skin or to the silicone coating 51 on the release liner 50, but still adhere firmly but releasably to film 30.

Alternatively, handle 10 can be electrostatically adhered to polymeric film 30, rather than through the use of an adhesive layer on the undersurface of handle 10. In such an embodiment, handle layers 10 and 20 as shown in the drawings comprise a layer of non-conductive material 10, e.g., a layer of polymeric film, and a layer of conductive material 20 (rather than a layer of adhesive). For example, a layer of aluminum 20 might be vapor deposited onto non-conductive polymeric film layer 10.

Optionally, conductive layer 20 may be disposed between two layers of non-conductive polymeric films, rather than having a single layer on only one side. However, only one non-conductive layer 20 is required, and handle 10-20 can be applied to polymeric film 30 with either conductive layer 20 applied directly against film 30, or with non-conductive layer 10 lying against film 30. The static change generated during handling of the materials in manufacture is sufficient to electrostatically bond handle 10-20 to film 30. An optional corona treatment may be used as a way to increase the electrostatic surface adhesion of the polymeric film, but it is not necessary.

A second electrostatic charge is created during the application process which enhances the electrostatic bond between handle 10-20 to polymeric film 30. This second electrostatic charge is generated when release liner 50 is peeled away from the adhesive layer 40 on the undersurface of film 30. Though not wishing to be bound by theory, when these two materials are separated, a positive charge will accumulate on the surface of the polyurethane and a negative charge on the release liner. Since two oppositely charged surfaces will attract each other, the positive static charge of polymeric film 30 is then attracted to the electron rich, negatively charged, conductive material 20. Therefore, this additional statically attractive force adds to the retention of handle 10-20 to polymeric film 30, and tends to remain until the user applies the system to the patient, at which time the system is grounded, thereby removing or at least diminishing the electrostatic attractive force.

Polymeric film 30 is preferably comprised of any breathable and waterproof material. In the preferred embodiment, a polymeric film on the order of from about 0.5 to about 4 mils (0.0005 to 0.004 inches) is preferred. The film is preferably very flexible, allowing it to conform readily to the user's skin or mucosa. The film must have sufficient strength to afford resistance to damage in handling and in use. It also preferably allows the passage of oxygen, thereby allowing the skin or mucosa to breathe. The polymeric film material preferably is a polyurethane film such as a Pebax® film (MediFilm 810, 2 mils, Mylan). Additionally, copolymers of polyethylene and vinyl acetate are also preferable.

The adhesive layer 40 may be any adhesive that bonds well to skin or mucosa. Preferably, a pressure sensitive adhesive is used. A type of adhesive found useful for adhesive layer 40 is a permanent acrylate-based pressure sensitive adhesive designed for skin, with a peel adhesion level of approximately 50 ounces. Other useful adhesives include, but are not limited to, silicone, urethane, synthetic rubber and natural rubber. Such adhesives can be formulated to adhere releasably to the silicone coated surface 51 of a release liner 50. At the same time, they can be formulated to adhere firmly to the patient's skin or mucosa such that polymeric film 30 will not peel away unless someone intends to do so. For example, one can use an acrylate derivative adhesive such as copolymers of alkyl acrylate/vinyl acetate containing —OH or/and —COOH functional groups, or hydrophobic styrenic rubber polymer or PIB containing 1 to 20% hydroattractants such as PVP, PVA, and cellulose derivatives such as Duro-Tak 87-2516 (National Starch), and PIB containing 20% Kollidong® CL-M (BASF).

The entire assembly of handle 10, adhesive layer 20, polymeric film 30 and adhesive layer 40 is releasably adhered to a release liner 50. Release liner 50 may be comprised of any material that will releasably adhere adhesive layer 40. However, in the preferred embodiment, release liner 50 is a paper material with a silicone coating 51 on the top surface thereof.

The very properties of polymeric film 30 which make it desirable in use make it difficult to handle in application. The drape and flexibility properties of polymeric film 30 may cause it to fold over onto itself and self-adhere relatively easily when one is trying to apply the system to the user's skin. The thicker handle 10 disclosed in the preferred embodiment reduces these shortcomings and makes the systems relatively easy to apply without fouling polymeric film 30. However, the structural characteristics of the stiffer and generally thicker material of handle 10 which aid in the application is compromised when a cut line 13 is made to handle 10 (FIG. 1). Cut line 13, which aids the applicator in the removal of handle 10, compromises the structural integrity of handle 10 and allows the polymeric film 30 to fold over and adhere to itself.

Edge release typically occurs with these systems when handle 10 is removed from polymeric film layer 30. The generally thicker material of handle 10 creates a lever arm out of handle 10 when handle 10 is being peeled off of film 30. This lever arm created by handle 10 acts to pry up film 30 from the patient's skin. If this force is great enough the edge of film 30 can separate from the patient's skin (e.g., edge release occurs). In general, as the stiffness of the material of handle 10 increases, the less flexible it becomes. The less flexible the handle becomes, the longer the lever arm becomes and this in turn creates higher forces which act upon film layer 30 causing more significant edge release. In addition, it is believed that as handle 10 is removed from polymeric film layer 30, it causes an electrostatic buildup in film layer 30, which contributes to the tendency of the edge of film 30 to release from and be pulled away from a patient's skin or mucosa. Therefore, the properties that make handle 30 useful, namely its stiffness, also create edge release.

The Angled Thumb Tab

Tab 11 is provided on handle 10 to minimize the tendency of film 30 to fold over at cut line 13, as well as aid in the removal of handle 10. Inwardly-projecting thumb tab 11 includes a distal portion 12. Preferably, the underside of thumb tab 11 is not coated with adhesive. In the preferred embodiment, the leading edge A of thumb tab 11 is disposed at an angle greater than 90 degrees with respect to the edge of the handle in the direction "B" in which the handle is pulled, and distal portion 12 extends beyond cut line 13 into window 15 of handle 10. Preferably, the angle is between about 120° and about 150°, and most preferably about 135°. This placement of distal portion 12 provides more support for polymeric film 30 and handle 10 and it is therefore less likely that polymeric film 30 will fold at cut line 13. However, this is merely the preferred embodiment and tab 10 may also be disposed outwardly. Similarly, it is preferably that cut line 13 extends between the edges of handle 10 at between about 130° and about 150°, most preferably about 135°, with respect to the direction in which handle 10 will be initially peeled away from film 30. This also helps prevent film 30 from buckling across the cut through the handle.

As described above, edge release typically occurs with these systems when handle 10 is removed from polymeric film layer 30. Tab 11 minimizes this tendency by reducing the mechanical advantage that handle 10 has over polymeric film 30 when handle 10 is being peeled off. The mechanical advantage is reduced by the angle at which thumb tab 11 projects from handle 10 and subsequently, the angle at which handle 10 is removed from polymeric film 30.

Interrupting the Continuity of Contact Between the, Handle and the Polymeric Film In addition to the mechanical advantages of thumb tab 11, edge release can also be minimized by interrupting the continuity of contact between the adhesive coated surface of handle 10 and the underlying non-adhesively coated surface of the polymeric film 30, at least in the vicinity of at least a portion of the edge of handle 10. Although not wishing to be bound by theory, it is believed that this interruption helps to minimize edge release in three ways:

1. less contact area means handle 10 can be removed more easily;
2. the mechanical advantage of the handle relative to the film 30 edge is reduced; and
3. localized electrostatic build up when handle 10 is peeled away from film 30 is reduced.

Interrupting the contact between the adhesive layer 20 of handle 10 and film 30 reduces the contact area. We have found it helpful to reduce the contact area by from about 10% to about 70%, preferably about 10% to about 50%, and most preferably from about 10% to about 30%, as compared to the contact area without such interruptions in continuity. If a greater reduction in contact area is desired, a more aggressive adhesive can be used in adhesive layer 20.

One technique for interrupting the adhesive layer of the handle and the non-adhesively coated surface of polymeric film 30 is to texture handle 10, at least at adhesive layer 20 on handle 10 which faces and is adhered to polymeric film 30. Preferably, this texturing is done by piercing slots 16 through handle 10 and adhesive coating layer 20 (FIGS. 1-6). Other techniques include placing pin holes through handle 10

(FIGS. 7, 8); knurling handle 10 (FIGS. 9, 10); embossing or debossing handle 10; printing adhesive layer 20 in a pattern (FIG. 11); and employing a handle material having a relatively rough surface facing polymeric film layer 30. Alternatively, the polymeric film 30 may be textured on the side facing handle 10 (FIG. 12). Preferably, the texturing is done in such a way as to break the adhesive coating layer itself, as distinguished from merely making it irregular in shape (see e.g., FIGS. 2, 4 and 8).

As depicted in FIG. 1, a first embodiment is shown utilizing a plurality of piercing slots 16 completely surrounding and angularly disposed with respect to window 15. The slots 16 may be pierced from the either side. However, in the preferred embodiment the slots are pierced from the top surface and through adhesive layer 20 on handle 10 as shown in FIG. 2.

In response to the piercing action, material of handle 10 at the pierced location is deflected toward polymeric film layer 30 resulting in a raised portion 17 of slot 16 (FIG. 2). Film 30 tends to bridge over raised portions 17 of slots 16, creating a "tunnel" at which film 30 is separated from handle 10. Raised portion 17 thereby effectively reduces the area of contact between film 30 and adhesive layer 20 of handle 10. This reduces the adhesive retention of handle 10 to polymeric film 30.

Figure 4:
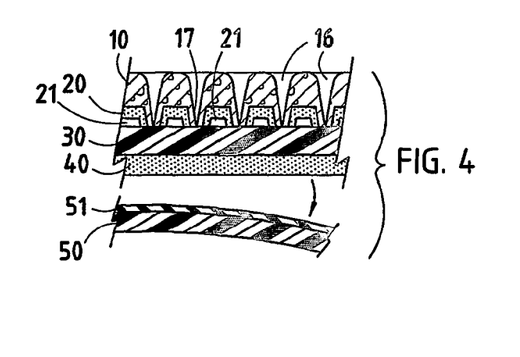
FIG. 4 is an enlarged sectional view of a wound dressing, ingredient delivery device, or IV hold-down of FIG. 2, taken at section IV of FIG. 2 with the release liner removed.

Also when handle 10 is removed from polymeric film 30 an atmospheric venting effect 21 occurs in the tunneling area (FIG. 4). This venting effect enhances the ease of removal of the handle. The result is less inadvertent edge release.

Additionally, raised portion 17 which is in contact with polymeric film 30 provides a conductive pathway between polymeric film 30 and handle 10. This pathway interrupts the continuity of contact between the adhesive coated surface 20 of handle 10 and the underlying non-adhesively coated surface of polymeric film 30 thereby minimizing the electrostatic buildup of localized electrostatic charge on the polyurethane film during the removal of handle 10. This minimization of electrostatic build up contributes towards the reduction in edge release.

Figure 5:
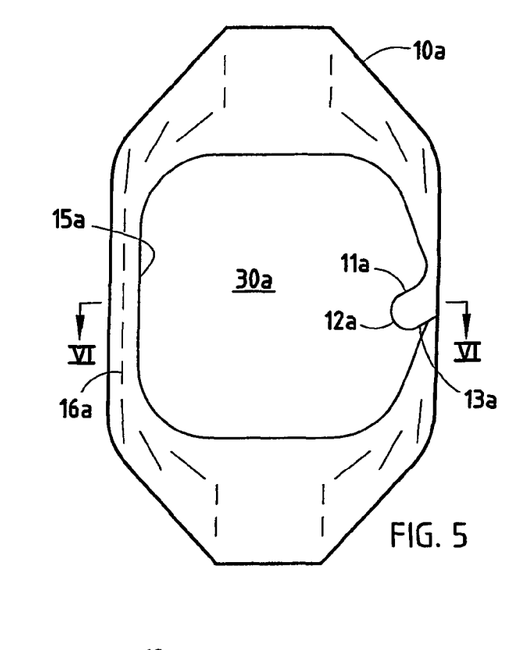
FIG. 5 is a plan view of a wound dressing, ingredient delivery device, or IV hold-down in accordance with a second embodiment of the present invention.
Figure 6:
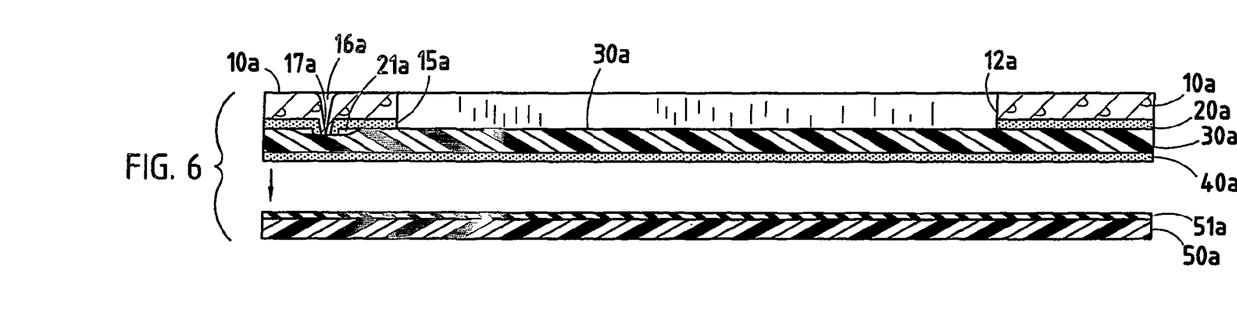
FIG. 6 is a cross sectional view of a wound dressing, ingredient delivery device, or IV hold-down of FIG. 5, taken along line VI-VI, with the release liner removed.

FIG. 5 shows a second embodiment including slots 16a which are parallel to window 15a along its sides, and angularly disposed with respect to the top and bottom surface. In this configuration, after the release liner 50a is removed, atmospheric venting effect 21a again occurs (FIG. 6).

Figure 7:
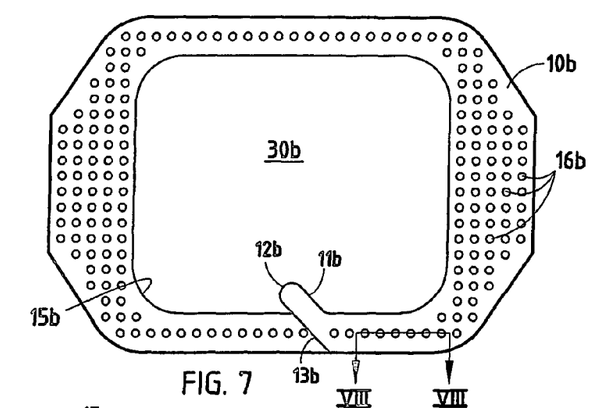
FIG. 7 is a plan view of a wound dressing, ingredient delivery device, or IV hold-down in accordance with a third embodiment of the present invention.
Figure 8:
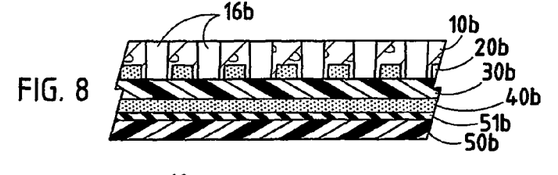
FIG. 8 is a cross sectional view of a wound dressing, ingredient delivery device, or IV hold-down of FIG. 7, taken along line VII-VII of FIG. 7.

A third embodiment is shown in FIG. 7 and is similar to the first two embodiments except that it utilizes a puncture or pinhole to interrupt the continuity between the handle 10b and the polymeric film 30b. As shown in FIG. 8, pinholes 16b minimize edge release by reducing the adhesion of handle 10b to the polymeric film 30b and also providing a conductive pathway between polymeric film 30 and handle 10 in order to minimize electrostatic buildup as described above.

Figure 9:
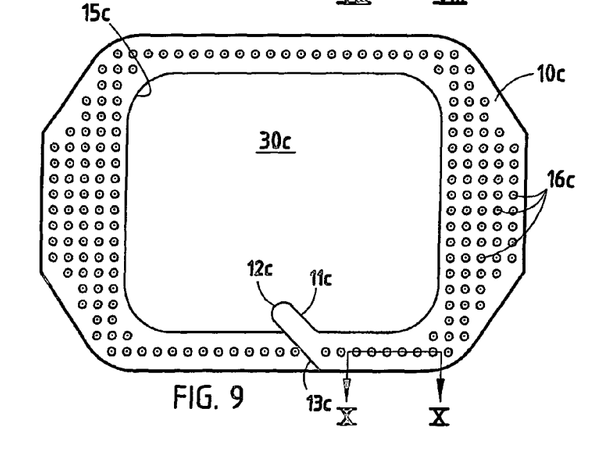
FIG. 9 is a plan view of a wound dressing, ingredient delivery device, or IV hold-down in accordance with a fourth embodiment of the present invention.
Figure 10:
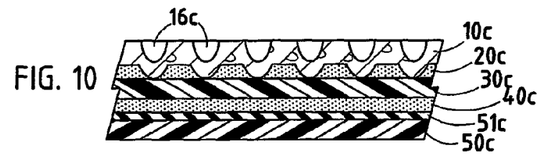
FIG. 10 is a cross sectional view of a wound dressing, ingredient delivery device, or IV hold-down of FIG. 9, taken along line X-X of FIG. 9.

A fourth embodiment using a knurled pattern is depicted in FIG. 9. The knurled pattern may take any geometrical shape and be either embossed or debossed on handle 10c. Additionally, the pattern may be varied thereby increasing or decreasing the contact area to accommodate the application requirements. Unique to this embodiment is the feature that the knurls 16c do not puncture handle 10c. Instead, the reduction in adhesion is accomplished through the bottom of knurls 16c residing directly on polymeric film layer 30c and therefore reducing the adhesive contact surface of polymeric film 30c, as shown if FIG. 10. However, this is not meant to be limiting and knurls 16c may puncture handle 10c if required. Embossing or debossing handles 10 is similar to knurling, though the raised portion would probably be larger in area than the knurl projections.

Figure 11:
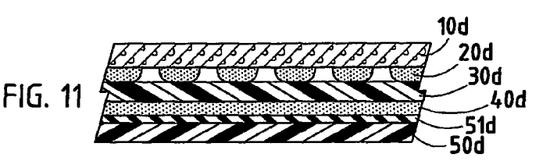
FIG. 11 is a cross sectional view of a wound dressing, ingredient delivery device, or IV hold-down in accordance with a fifth embodiment of the present invention.
Figure 12:
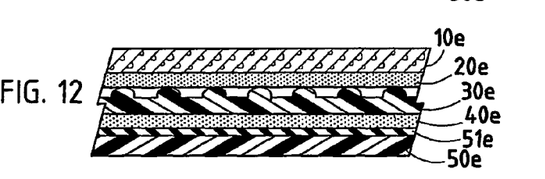
FIG. 12 is a cross sectional view of a wound dressing, ingredient delivery device, or IV hold-down in accordance with a sixth embodiment of the present invention.

Additionally, a fifth embodiment is shown in FIG. 11. This embodiment reduces the adhesion between handle 10d and polymeric film layer 30d by patterning the adhesive layer. As described above, the pattern may be varied thereby increasing or decreasing the contact area according to the specific requirements of the application.

Still further, it is possible to accomplish this reduction in continuity through the use of a rough surface or handle 10, facing polymeric film layer 30. This can be done, for example, through the use of a rough or non-smooth paper for handle 10.

FIG. 12 shows a sixth embodiment which uses a polymeric film layer 30e having at least a textured upper surface to reduce the continuity of contact between handle 10e and polymeric film 30e. The pattern may take any geometrical shape and be either embossed or debossed on polymeric film layer 30e. Additionally, as described above, the pattern may be varied thereby increasing or decreasing the contact area to accommodate the application requirements. The patterning of polymeric film layer 30e may be accomplished mechanically or chemically.

While the embodiments described above are wound dressings or IV hold-down devices, the various aspects of the present invention are also applicable to devices designed to deliver active ingredients to or through the dermal or mucosal layers. Such delivery systems typically deliver the active via a gel modulated system, membrane modulated system, or an adhesive modulated system. All of the embodiments of FIGS. 1-19 can be made to be ingredient delivery devices by incorporating an active ingredient into adhesive layer 40-40j, for example.

Figure 14:
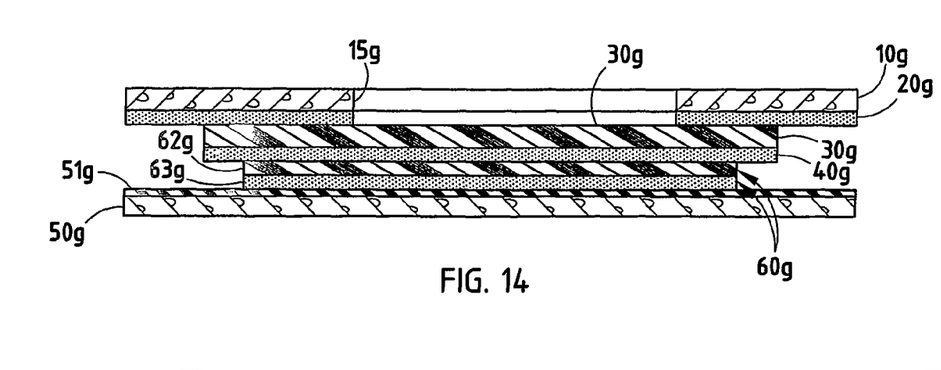
FIG. 14 is a cross sectional of a wound dressing, ingredient delivery device, or IV hold-down in accordance with an eighth embodiment of the present invention.
Figure 15:
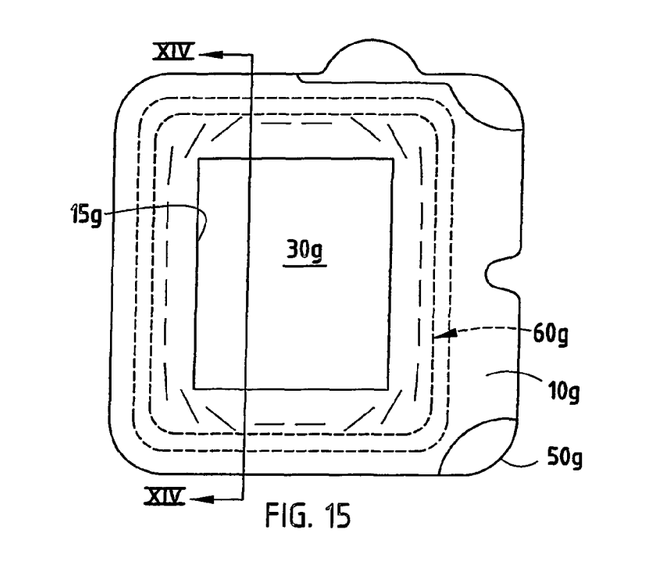
FIG. 15 is a plan view of a wound dressing, ingredient delivery device, or IV hold-down of FIG. 14.

The delivery system depicted in FIG. 14 includes a breathable and waterproof polymeric film 30g. Layered to a first side of film 30g is adhesive layer 40g. Adhered to adhesive layer 40g of film 30g is an active ingredient containing island 60g. Island 60g comprises a thin or ultra thin polymeric backing film 62g. Layered to backing film 62g is an active ingredient layer 63g that may or may not be incorporated into an adhesive.

Incorporating an Anti-Static Ingredient

Figure 13:
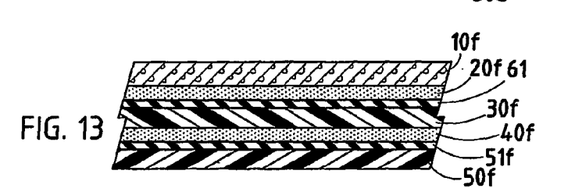
FIG. 13 is a cross sectional view of a wound dressing, ingredient delivery device, or IV hold-down in accordance with a seventh embodiment of the present invention.

Edge release can also be minimized by utilizing an anti-static coating to minimize the electrostatic buildup that occurs when handle 10 is removed. A seventh embodiment using an anti-static coating 61 is shown in FIG. 13. The anti-static coating layer 61 on polymeric film layer 30f acts to minimize the electrostatic buildup of localized electrostatic charge on polyurethane film 30f during the removal of the handle 10f. The minimization of electrostatic build up contributes towards the reduction in edge release. Alternatively, or in addition, anti-static material may be incorporated onto the lower surface of polyurethane film 30f or into adhesive layer 40f of polyurethane film 30f.

Removing a Portion of Handle or Adhesive at the Periphery

Removing a portion of handle 10, or its underlying adhesive layer 20, from over at least a portion of the edge area of film layer 30 helps to minimize edge release. Although not wishing to be bound by theory, it is believed that this is accomplished in three ways:

1. less adhesive contact area means handle 10 can be removed more easily;
2. reducing the ability of handle 10 to act as a lifting lever relative to film 30, at least when a portion of the handle per se is removed; and
3. minimizing the localized electrostatic build up at the periphery of film 30 when handle 10 is peeled from film 30, by moving the periphery of handle 10 away from the edge of film 30.

Figure 16:
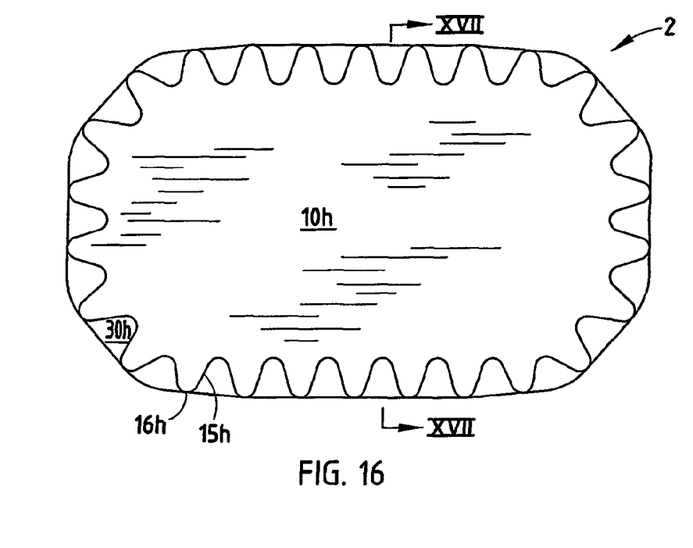
FIG. 16 is a plan view of a wound dressing, ingredient delivery device, or IV hold-down.
Figure 17:
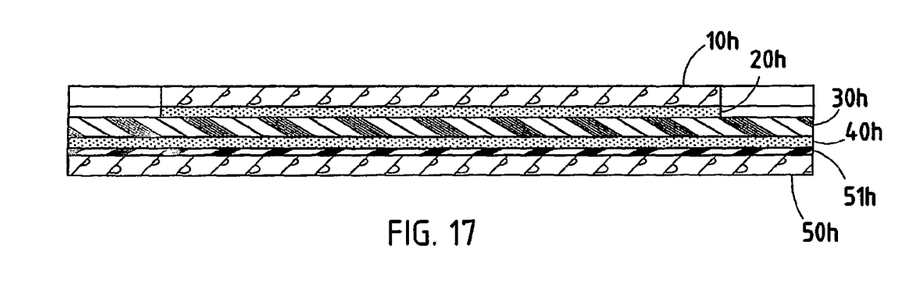
FIG. 17 is a cross sectional view of the wound dressing, ingredient delivery device, or IV hold-down of FIG. 16, taken along line XVII-XVII of FIG. 16.

One way to move at least a portion of the edge of said handle away from the periphery of said polymeric film is to pattern the handle layer with a scalloped pattern as shown in FIGS. 16 and 17. In this embodiment, the scalloping extends around the entire perimeter of handle 10. The scalloped edge reduces the mechanical advantage of handle 10 primarily in two ways. The first is by reducing the surface area of adhesive coating 20 disposed on the periphery of handle 10, and the second is by reducing the ability of handle 10 to act as a lever. In the first mode, a portion of the periphery of handle 10 is removed resulting in scalloped edge 15. Simultaneous to this removal of a portion of handle 10 is the removal of a corresponding portion of adhesive coating 20 attached thereto. This removal of adhesive 20 on the periphery of handle 10 reduces the upward force exerted on the periphery of polymeric film 30 by adhesive coating 20 during its removal. Reducing the upward force exerted on the periphery of polymeric film 30 reduces edge lift. In the second mode, scalloped edge 15 reduces the ability of the generally thicker material of handle 10 to act as a lever arm.

When the peripheral interaction between adhesive layer 20 and polymeric film 30 is removed, the localized electrostatic buildup on film 30 is also reduced. This is because the interaction between adhesive layer 20 and film layer 30, during their separation, causes the electrostatic buildup. The removal of a portion of the peripheral edge of handle 10, and subsequently adhesive layer 20, or the removal of some of the adhesive at the edges of handle 10 minimizes the electrostatic buildup on the peripheral edge of polymeric film 30 by removing this interaction and therefore, reduces edge lift.

The scalloped edge (15) of handle 10 is depicted in FIG. 16 as having a wave like or sinusoidal like pattern, leaving projecting portions 16 extending to the edge of film layer 30. Other geometrical forms may be used which reduce the interaction between the periphery of handle 10 and the periphery of film 30. While a handle could be made that simply does not extend to the edge of film layer 30, thereby reducing edge lift, the scalloped pattern has the advantage of having end portions 16 that extend to the edge of film 30. End portions 16 act to support thin film 30 and keep it from folding over onto itself during application. Therefore, scalloped edge 15 retains the benefits of a handle layer (e.g., ease of application) while minimizing the negative effects of a handle layer (e.g., edge lift).

Figure 18:
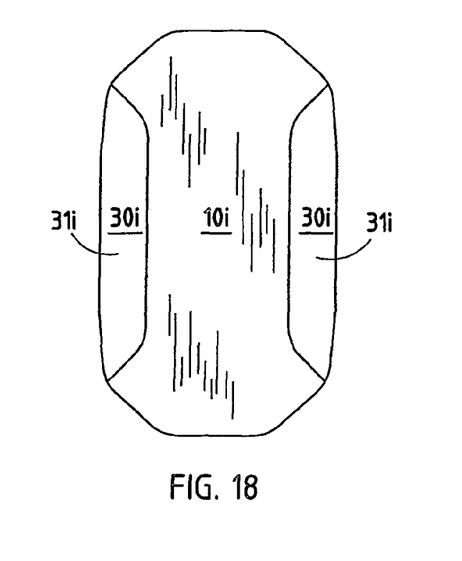
FIG. 18 is a plan view of a wound dressing, ingredient delivery device, or IV hold-down in accordance with a tenth embodiment of the present invention.
Figure 19:
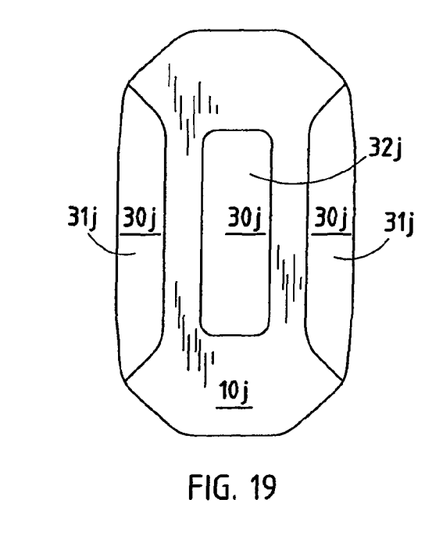
FIG. 19 is a plan view of a wound dressing, ingredient delivery device, or IV hold-down in accordance with an eleventh embodiment of the present invention.

In the FIG. 18 embodiment, the edge portion of handle 10 along two opposite sides thereof, preferably the longest sides, have been substantially removed as a continuous, uninterrupted strip. This leaves the longest edge portions 31 of polymeric film but retains a portion of handle 10 along two other sides which extends to the film periphery sides to support film 30 during application. Preferably, only the central portion of the edge of handle 10 is removed, such that end or corner portions 11 of handle 10 extend out to the edges or corners to give stability. The FIG. 19 embodiment is similar to the FIG. 18 version, but also incorporates a window of removed handle material which is centrally located on the dressing, leaving the central portion 32 of film 30 also exposed.

Although only a few preferred embodiments have been shown and described it is envisioned that there are numerous geometrical patterns that may used. Additionally, there are supplementary methods which can be combined with the various edge geometries for reducing the edge lift even further. For example, the preferred embodiment may include additional features such as texturing handle 10, texturing adhesive layer 20, texturing polymeric film layer 30 and/or using an anti-static ingredient in one of, the adhesive coating on the underside of the polymeric film, or on the upper or lower surface of the polymeric film itself. Additionally, texturing may be done by piercing slots, placing pin holes, knurling, embossing or debossing, or creating a relatively rough surface on handle 10.

CONCLUSION

The embodiments described above minimize the problem of edge release which typically occurs in adhesive devices used as wound dressings, ingredient delivery devices and IV hold-downs. Of course it is understood that the above are preferred embodiments only, and that various changes and alterations can be made without departing from the spirit and scope of the invention as set forth in the appended claims, as interpreted in accordance with the principles of patent law.

The invention claimed is:

1. A wound dressing, ingredient delivery device or IV hold-down comprising:
    a handle defining an outer peripheral edge and an inner peripheral edge forming a window through the handle, the handle including a cut extending between and interconnecting the inner and outer peripheral edges;
    a polymeric film having a first and second side, at least a portion of said first side of the polymeric film being coated with an adhesive layer;
    the handle being adhered to said second side of said polymeric film, the continuity of contact between the handle and the underlying second surface of the polymeric film being interrupted at least in the vicinity of at least a portion of the edge of the handle by a plurality of deformations in the handle forming a plurality of regions wherein the handle is spaced-apart from the film to define a plurality of tunnels.

2. The device of claim 1, wherein:
the deformations in the handle comprise slots.

3. The device of claim 2, wherein:
at least some of the slots are parallel to one another.

4. The device of claim 1, wherein:
the window through the handle is generally quadrilateral in shape.

5. The device of claim 4, wherein:
the inner peripheral edge defines a pair of spaced-apart linear inner edge portions that are parallel to one another, and wherein the outer peripheral edge defines a pair of linear outer edge portions that are parallel to the linear inner edge portions to form a pair of spaced-apart elongated handle portions between the linear inner and outer edge portions.

6. The device of claim 5, wherein:
the deformations in the handle comprise a plurality of parallel slots through the elongated handle portions.

7. The device of claim 1, wherein:
the handle includes a tab extending into the window immediately adjacent the cut.

8. The device of claim 7, wherein:
the tab defines a side edge immediately adjacent the cut facing a portion of the inner peripheral edge on an opposite side of the cut relative to the tab, and wherein:
the side edge of the tab and the portion of the inner peripheral edge define an angle therebetween that is substantially less than ninety degrees.

9. The device of claim 1, wherein:
the handle defines an undersurface, at least a portion of which is coated with an adhesive that adheres the handle to the second side of the polymeric film.

10. The device of claim 1, wherein:
the handle defines an undersurface that is substantially free of adhesives, and wherein the handle is adhered to the polymeric film by an electrostatic force.

11. The device of claim 10, wherein:
the handle comprises a layer of conductive material.

12. The device of claim 11, wherein:
the handle further comprises a layer of non-conductive material.

13. A wound dressing, ingredient delivery device or IV hold-down comprising:
a handle defining an outer peripheral edge extending around substantially the entire handle;
a polymeric film having a first and second side, at least a portion of the first side of the polymeric film being coated with an adhesive layer;
the handle being adhered to the second side of said polymeric film, the continuity of contact between the handle and the underlying second surface of the polymeric film being interrupted at least in the vicinity of at least a portion of the edge of the handle by a plurality of discrete openings in the handle defining edges that do not connect to the outer peripheral edge of the handle.

14. The device of claim 13, wherein:
the discrete openings comprise pinholes.

15. The device of claim 14, wherein:
the pinholes are generally circular.

16. The device of claim 13, wherein:
the discrete openings comprise elongated slots.

17. The device of claim 13, wherein:
the handle defines an undersurface, at least a portion of which is coated with an adhesive that adheres the handle to the second side of the polymeric film.

18. The device of claim 13, wherein:
the handle defines an undersurface that is substantially free of adhesives, and wherein the handle is adhered to the polymeric film by an electrostatic force.

19. The device of claim 18, wherein:
the handle comprises a layer of conductive material.

20. The device of claim 19, wherein:
the handle further comprises a layer of non-conductive material.

21. The device of claim 13, wherein:
the handle includes an inner peripheral edge forming a window through the handle, the handle including a cut extending between and interconnecting the inner and outer edges.

22. The device of claim 21, wherein:
the handle includes a tab extending into the window immediately adjacent the cut.

23. The device of claim 22, wherein:
the tab defines a side edge immediately adjacent the cut facing a portion of the inner peripheral edge on an opposite side of the cut relative to the tab, and wherein:
the side edge of the tab and the portion of the inner peripheral edge define an angle therebetween that is substantially less than ninety degrees.

24. The device of claim 21, wherein:
the inner peripheral edge defines a pair of spaced-apart linear inner edge portions that are parallel to one another, and wherein the outer peripheral edge defines a pair of linear outer edge portions that are parallel to the linear inner edge portions to form a pair of spaced-apart elongated handle portions between the linear inner and outer edge portions.

25. The device of claim 24, wherein:
the deformations in the handle comprise a plurality of parallel slots through the elongated handle portions.

26. A wound dressing, ingredient delivery device or IV hold-down comprising:
a handle;
a polymeric film having first and second sides, wherein at least a portion of the first side of the polymeric film is coated with an adhesive material;
the handle being electrostatically adhered to the second side of the polymeric film without adhesive material, the handle defining an outer peripheral edge extending around substantially the entire handle, and including an enlarged opening through a central portion of the handle defining an inner edge that is spaced-apart from the outer edge, the handle including a first cut through the handle connecting the outer edge of the handle to the inner edge, and a plurality of second cuts through the handle disposed about the enlarged opening, and wherein the second cuts are not connected to either the outer peripheral edge or to the inner edge; and
the handle comprises a layer of the non-conductive material and a layer of conductive metal material.

27. The device of claim 26, wherein:
at least some of the second cuts are parallel to one another.

28. The device of claim 26, wherein:
the enlarged opening is substantially quadrilateral in shape.

29. The device of claim 28, wherein:
the inner peripheral edge defines a pair of spaced-apart linear inner edge portions that are parallel to one another, and wherein the outer peripheral edge defines a pair of linear outer edge portions that are parallel to the linear inner edge portions to form a pair of spaced-apart elongated handle portions between the linear inner and outer edge portions.

30. The device of claim 26, wherein:
the handle includes a tab extending into the enlarged opening immediately adjacent the first cut.

31. The device of claim 30, wherein:
the tab defines a side edge immediately adjacent the cut facing a portion of the inner edge on an opposite side of the cut relative to the tab, and wherein:
the side edge of the tab and the portion of the inner edge define an angle therebetween that is substantially less than ninety degrees.

* * * * *

UNITED STATES PATENT AND TRADEMARK OFFICE
CERTIFICATE OF CORRECTION

| | | |
|---|---|---|
| PATENT NO. | : 7,888,546 B2 | |
| APPLICATION NO. | : 10/563340 | |
| DATED | : February 15, 2011 | |
| INVENTOR(S) | : Marcoux et al. | |

It is certified that error appears in the above-identified patent and that said Letters Patent is hereby corrected as shown below:

Column 2
Line 44 "VII-VII" should be --VIII-VIII--

Column 6
Line 37 "the, Handle" should be --the Handle--

Signed and Sealed this
Twenty-eighth Day of June, 2011

David J. Kappos
*Director of the United States Patent and Trademark Office*